United States Patent
Augustyns et al.

(10) Patent No.: US 11,166,967 B2
(45) Date of Patent: Nov. 9, 2021

(54) BIS(ACETAMIDOPHENYL) GUANIDINOPHENYLETHYLPHOSPHONATES FOR USE IN THE PREVENTION AND/OR TREATMENT OF PAR-RELATED DISEASES

(71) Applicant: Universiteit Antwerpen, Antwerp (BE)

(72) Inventors: Koen Augustyns, Wilrijk (BE); Jurgen Joossens, Wilrijk (BE); Pieter Van Der Veken, Wilrijk (BE); Paul Cos, Wilrijk (BE); Cedric Joossen, Wilrijk (BE); Benedicte Yvonne De Winter, Wilrijk (BE); Hannah Ceuleers, Wilrijk (BE); Hanne Van Spaendonk, Wilrijk (BE)

(73) Assignee: Universiteit Antwerpen, Antwerp (BE)

( * ) Notice: Subject to any disclaimer, the term of this patent is extended or adjusted under 35 U.S.C. 154(b) by 0 days.

(21) Appl. No.: 16/301,240

(22) PCT Filed: May 18, 2017

(86) PCT No.: PCT/EP2017/061933
§ 371 (c)(1),
(2) Date: Nov. 13, 2018

(87) PCT Pub. No.: WO2017/198753
PCT Pub. Date: Nov. 23, 2017

(65) Prior Publication Data
US 2019/0175629 A1  Jun. 13, 2019

(30) Foreign Application Priority Data
May 19, 2016 (EP) .................................... 16170402

(51) Int. Cl.
*A61K 31/688* (2006.01)
*A61P 27/04* (2006.01)
*A61P 25/04* (2006.01)

(52) U.S. Cl.
CPC ............ *A61K 31/688* (2013.01); *A61P 25/04* (2018.01); *A61P 27/04* (2018.01)

(58) Field of Classification Search
CPC .................................................. A61K 31/688
See application file for complete search history.

(56) References Cited

U.S. PATENT DOCUMENTS

| | | | |
|---|---|---|---|
| 6,369,086 B1 | 4/2002 | Davis et al. | |
| 6,369,087 B1 | 4/2002 | Whittle et al. | |
| 6,372,733 B1 | 4/2002 | Caldwell et al. | |
| 6,372,778 B1 | 4/2002 | Tung et al. | |
| 8,003,627 B2 * | 8/2011 | Augustyns ............ | C07F 9/4084 514/119 |

FOREIGN PATENT DOCUMENTS

| | | |
|---|---|---|
| WO | 2007045496 A1 | 4/2007 |
| WO | 2014140299 A1 | 9/2014 |

OTHER PUBLICATIONS

Takei-Taniguchi et al. Journal of Dermatology 2012, 39, 625-631 (Year: 2012).*
Smith et al. Arch Dermatol 2012, 148, 1395-1398 (Year: 2012).*
Ulisse et al. Current Cancer Drug Targets 2009, 9, 32-71 (Year: 2009).*
Manaviatetal. BMC Ophthalmology 2008, 8:10, pp. 1-4 (Year: 2008).*
Deiteren, A. et al; "Histamine H4 and H1 receptors contribute to postinflammatory visceral hypersensitivity"; Gut 63 (12); pp. 1873-1882; Feb. 21, 2014.
Deiteren, A., et al; "P2X3 Receptors Mediate Visceral Hypersensitivity during Acute Chemically-Induced Colitis and in the Post-Inflammatory Phase via Different Mechanisms of Sensitization"; PLoS One 10(4); pp. 1-17; Apr. 17, 2015.
Hu, J. et al; "Serine Protease Inhibitor A3K Protects Rabbit Corneal Endothelium From Barrier Function Disruption Induced by TNF-alpha"; Investigative Ophthalmology & Visual Science; pp. 5400-5407 (2013).
Joossen, C. et al; "Optimization and validation of an existing, surgical and robust dry eye rat model for the evaluation of therapeutic compounds"; Experimental Eye Research 146; pp. 172-178; (2016).
Joossens, J. et al; "Small, Potent, and Selective Diaryl Phosphonate Inhibitors for Urokinase-Type Plasminogen Activator with In Vivo Antimetastatic Properties"; Journal of Medicinal Chemistry 50; pp. 6638-6646 (2007).
Lin, Z. et al; "Serine Protease Inhibitor A3K Suppressed the Formation of Ocular Surface Squamous Metaplasia in a Mouse Model of Experimental Dry Eye"; Investigative Ophthalmology & Visual Science 55; pp. 5813-5820 (2014).
Ness, T.J., et al.; "Colorectal distension as a noxious visceral stimulus: physiologic and pharmacologic characterization of pseudaffective reflexes in the rat"; Brain Research 450; pp. 153-169 (1988).
Thomae, E. et al; "First In-111-labeled activity-based probe for SPECT imaging of uPA activity: in vivo study in human cancer xenografts"; J Labelled Compd Radiopharm 58; S104-S104 (2015).
Vermeulen, W., et al; "Role of TRPV1 and TRPA1 in visceral hypersensitivity to colorectal distension during experimental colitis in rats"; European Journal of Pharmacology; 698(1-3); pp. 404-412; (2013).
European Patent Office International Search Report and Written Opinion dated Sep. 8, 2017 in reference to International Application No. PCT/EP2017/061933 filed May 18, 2017.
European Patent Office Extended Search Report dated Nov. 9, 2016 in reference to European Patent Application No. 16170402.8 filed May 19, 2016.

\* cited by examiner

*Primary Examiner* — Matthew P Coughlin
(74) *Attorney, Agent, or Firm* — Dinsmore & Shohl LLP

(57) ABSTRACT

The present invention relates to compounds for use in the prevention and/or treatment of PAR-related diseases, such as for example: pain and ocular disorders. More in particular, the present invention provides bis(acetamidophenyl) guanidinophenylethylphosphonates for use in the prevention and/or treatment of pancreatitis-related pain, IBS (irritable bowel syndrome), IBD (inflammatory bowel disease), dry eye disease and conjunctivitis sicca. These inhibitors were found to have a different inhibitory profile compared to diphenyl guanidinophenylethylphosphonates leading to a more pronounced effect on these conditions.

5 Claims, 7 Drawing Sheets

Fig. 1A Post-colitis + 0.01 mg/kg cm pd-4
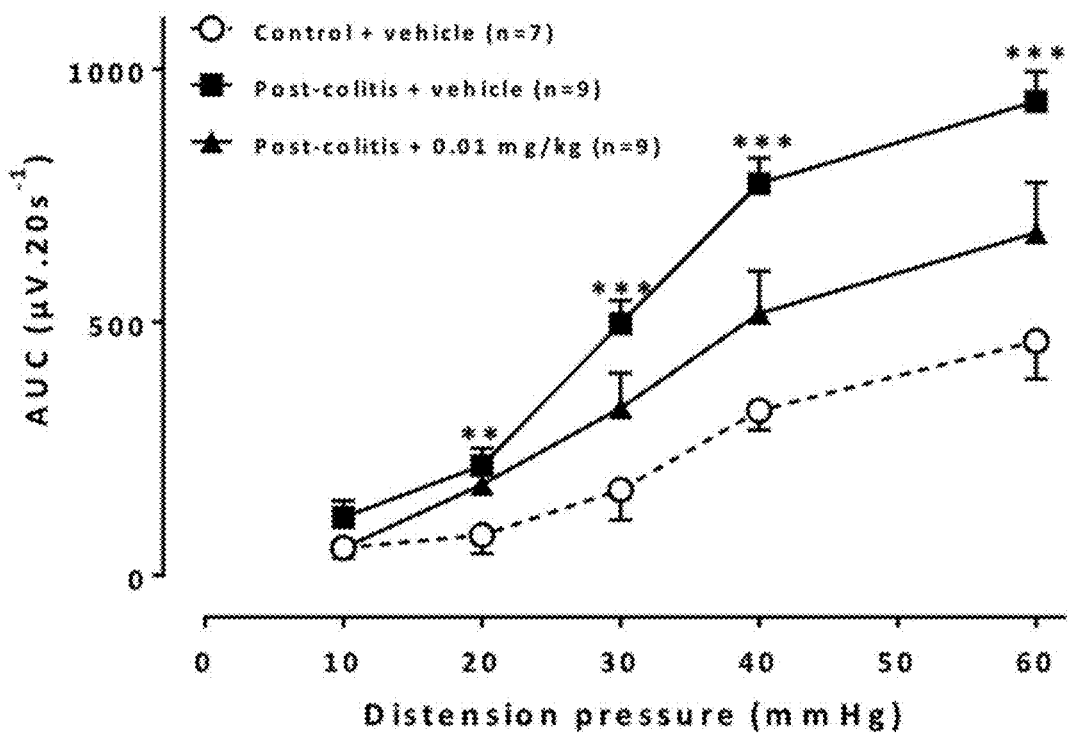
Fig. 1B Post-colitis + 0.1 mg/kg cm pd-4
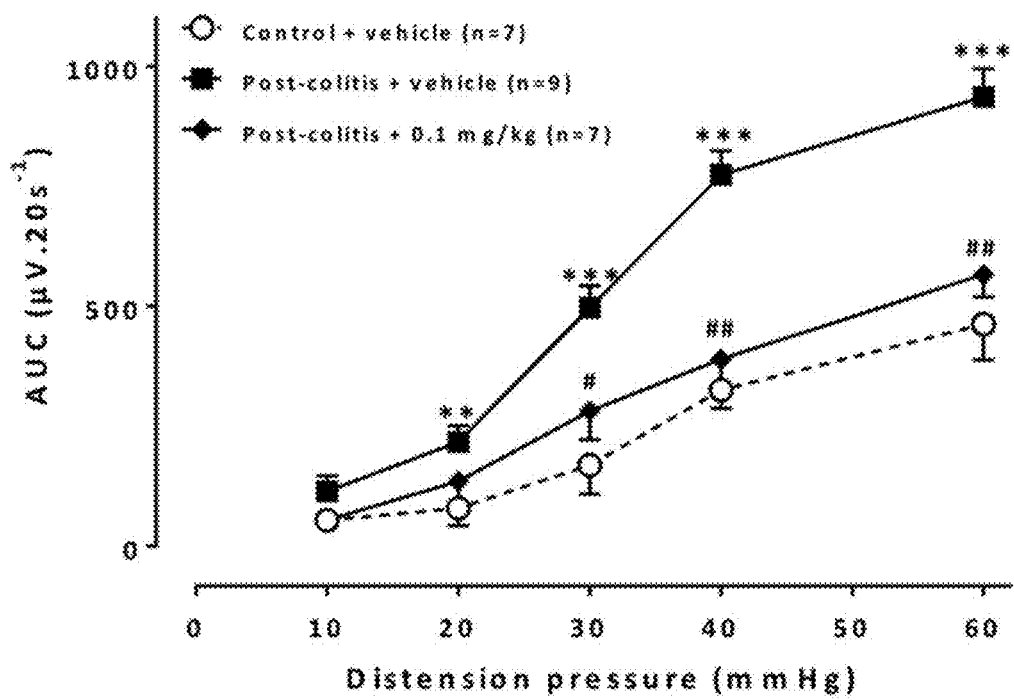

Fig. 1C Post-colitis + 1 mg/kg cm pd-4
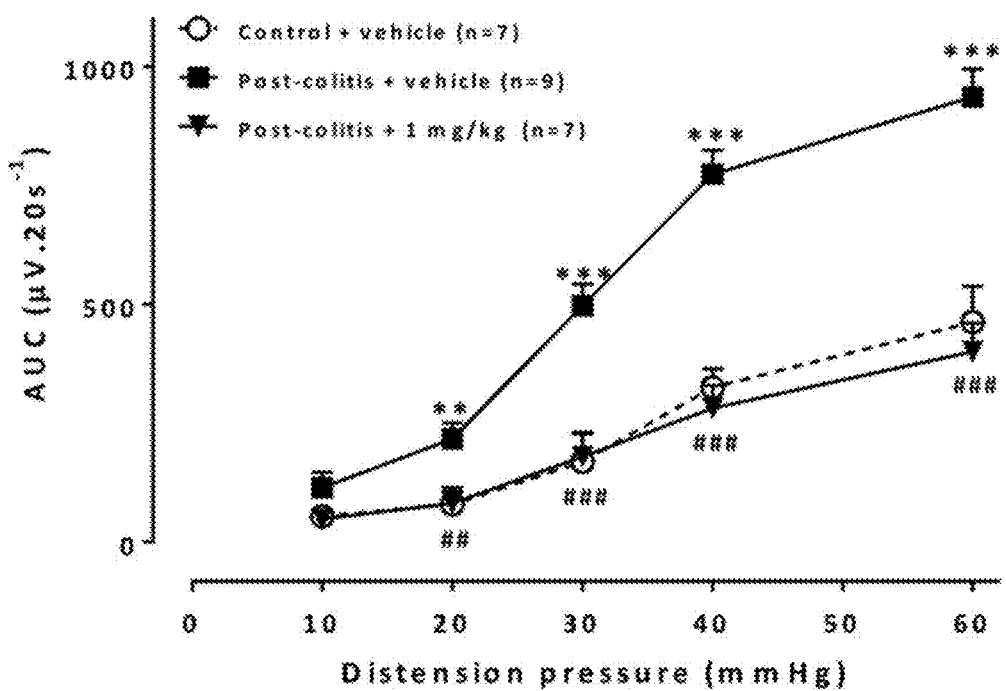
Fig. 1D Control + 1 mg/kg cm pd-4
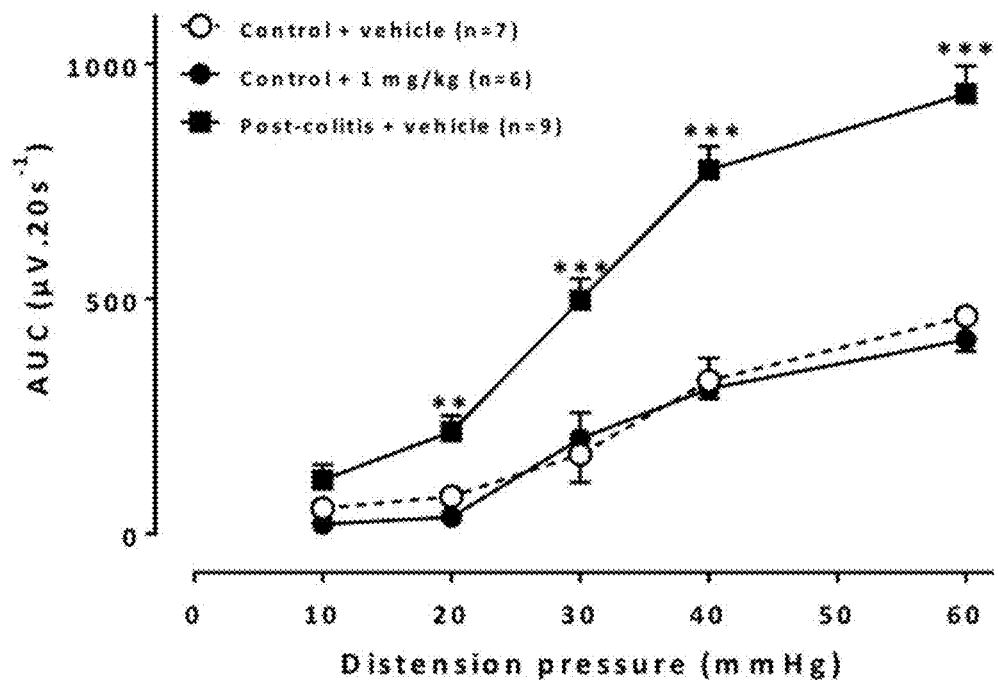

Fig. 2
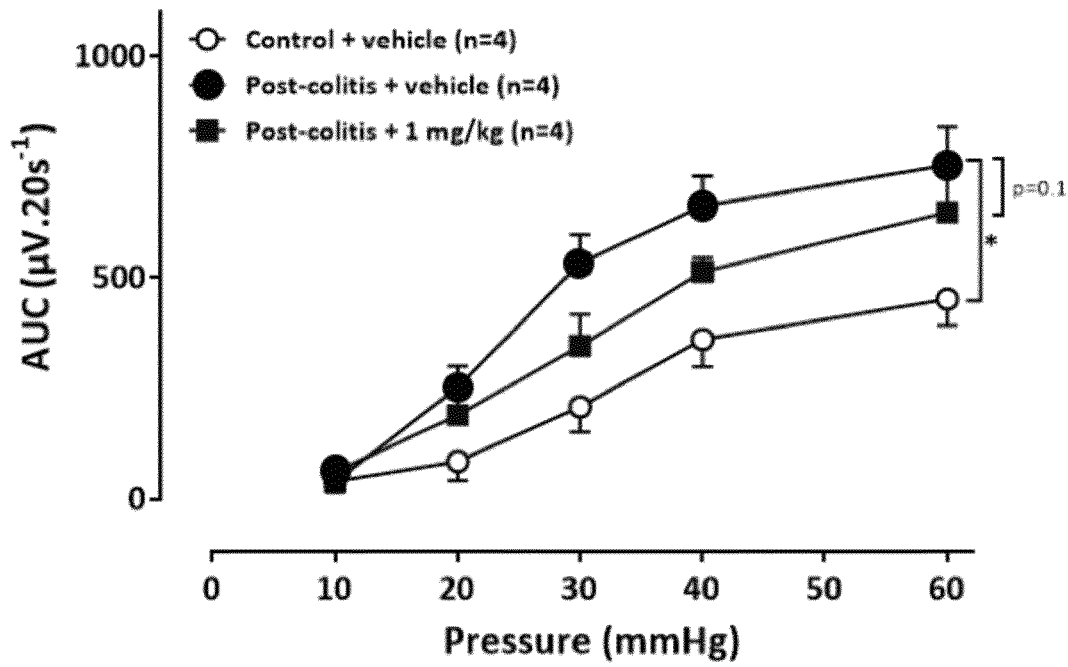
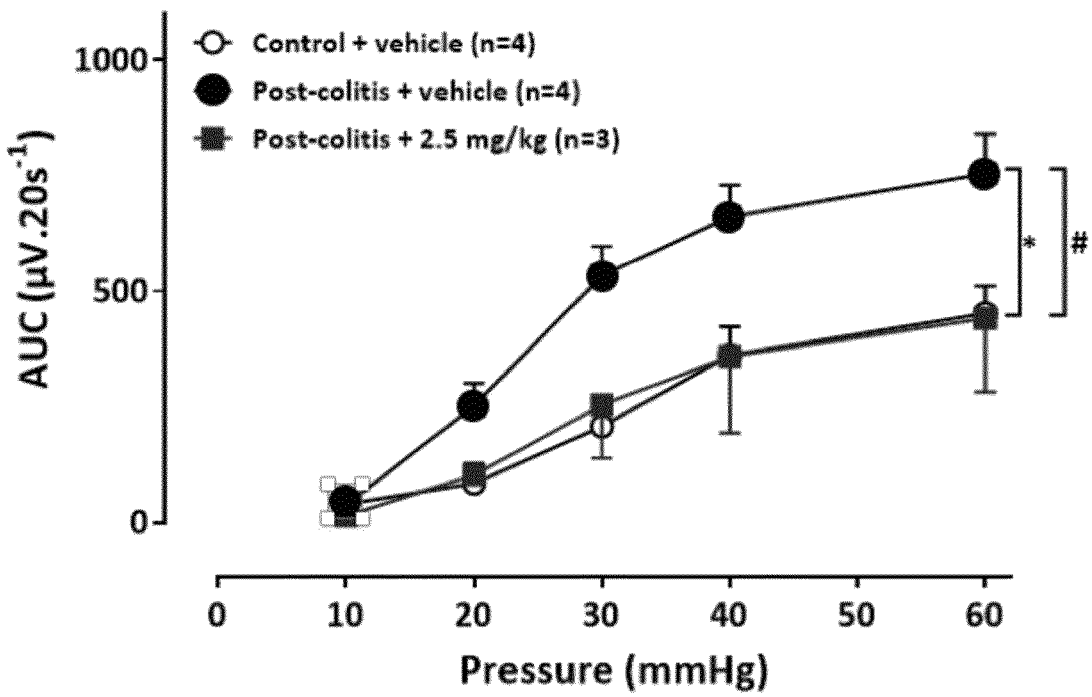

BIS(ACETAMIDOPHENYL) GUANIDINOPHENYLETHYLPHOSPHONATES FOR USE IN THE PREVENTION AND/OR TREATMENT OF PAR-RELATED DISEASES

FIELD OF THE INVENTION

The present invention relates to compounds for use in the prevention and/or treatment of PAR-related diseases, such as for example: pain and ocular surface diseases. More in particular, the present invention provides bis(acetamidophenyl) guanidinophenylethylphosphonates for use in the prevention and/or treatment of pancreatitis-related pain, IBS (irritable bowel syndrome), IBD (inflammatory bowel disease), dry eye disease and conjunctivitis sicca. These inhibitors were found to have a different inhibitory profile compared to diphenyl guanidinophenylethylphosphonates leading to a more pronounced effect on these conditions.

BACKGROUND TO THE INVENTION

The present invention is based on the finding that bis(acetamidophenyl) guanidinophenylethylphosphonate compounds are highly useful in the treatment of PAR-related (Protease Activated Receptor) disorders, more in particular PAR2-related disorders. PAR2 has a unique activation mechanism and is the common target of multiple proteolytic enzymes involved in many biological functions. PAR2 is described in several types of pain, ocular surface diseases, tissue damage, skin disorders, respiratory disorders, and gastrointestinal disorders. Reported enzymes for PAR2 activation include: mast cell tryptase, KLK2, KLK4, KLK5, KLK6, KLK14, TMPRSS2, trypsin IV, matriptase/MT-SP1.

Hence, it is to be expected that in the treatment of PAR-related disorders, or more specifically PAR2-related disorders, a multi-target compound is needed in order to target several of the PAR activating enzymes simultaneously. Indeed, we have found a set of serine protease targeting compounds, having the correct multi-target biochemical and physicochemical profile to reduce PAR activation in multiple in vivo models. Indeed, and as evident from the examples herein below, the compounds disclosed herein, were found to be highly useful in the treatment of PAR-related disorders such as pain, ocular surface diseases, tissue damage, skin disorders, respiratory disorders, gastrointestinal disorders.

With respect to pain, in particular visceral pain or hypersensitivity is a well-known problem in e.g. the IBS (irritable bowel syndrome), IBD (inflammatory bowel disease) and pancreatitis population. Currently no therapeutic strategies are available that work through normalizing the visceral pain sensation. The presence of huge unmet needs is a result of the lack of a significant number of drugs approved by the FDA and the use of off-label drugs, which cause several adverse side effects such as severe chronic idiopathic constipation, ischemic colitis, abdominal discomfort and pain, nausea, GI discomfort and pain, headache, dizziness, diarrhea, and hepatic dysfunction. In the field of IBS, pain hypersensitisation is the most important unmet need. There are only four approved medications for the treatment of irritable bowel syndrome in the market: Lotronex, Amitiza, Linzess or Constella, and Iribo. Serine proteases are generally known to be involved in gastrointestinal diseases, but as far as we know and until now no small drug-like molecule serine protease inhibitor has shown a therapeutically relevant effect in an in vivo model related to visceral pain specifically.

With respect to ocular disorders, more in particular ocular surface diseases such as dry eye, allergic keratoconjunctivitis, infection, and chemical injury are common disease conditions. Serine proteases are generally known to be involved in ocular surface diseases, but until now no small molecule serine protease inhibitor has shown a strong effect in an in vivo model related to ocular surface disease.

We have now identified the bis(acetamidophenyl) guanidinophenylethylphosphonate motive as the chemical template with the ideal inhibition profile and physicochemical properties for the treatment of PAR-related disorders, more in particular pain (hypersensitivity) in the gastrointestinal tract and ocular disorders. Generally diphenyl guanidinophenylethylphosphonates are described as potent and selective uPA inhibitors and they showed very strong antimetastatic effects in in vivo models (Joossens et al., 2007). This template was also used to develop activity based probes towards tumor imaging (Thomae et al., 2015).

In the same studies these diphenyl guanidinophenylethylphosphonates were modified towards bis(acetamidophenyl) guanidinophenylethylphosphonate to avoid possible cytotoxic effects by releasing a paracetamol moiety instead of a phenol moiety. Until now, no hints were made that the shift from a diphenyl guanidinophenylethylphosphonates scaffold towards a bis(acetamidophenyl) guanidinophenylethylphosphonate could lead to a different therapeutic application.

Nevertheless, we present here for the first time the in vitro and in vivo proof that the shift of diphenyl guanidinophenylethylphosphonates towards bis(acetamidophenyl) guanidinophenylethylphosphonates could lead to a different therapeutic application. Even more, the slightly different inhibition profile is convincingly depicted in table I presenting the difference in inhibition profile between the diphenyl guanidinophenylethylphosphonate and the bis(acetamidophenyl) guanidinophenylethylphosphonates.

We have evaluated different diphenyl guanidinophenylethylphosphonates and bis(acetamidophenyl) guanidinophenylethylphosphonates against a panel of serine proteases: uPA, tPA, thrombin, plasmin, FXIIa, FXa, cathepsinG, HNE, KLK1, KLK2, KLK4, KLK8, PLKLK, tryptase, matriptase, chymotrypsin and chymase. Diphenyl guanidinophenylethylphosphonates show significantly less inhibition towards matriptase, tryptase and cathepsinG compared to their bis(acetamidophenyl) guanidinophenylethylphosphonates analogues. This difference in biochemical profile but also the possible difference in the physicochemical profile, makes them more useful in the treatment of PAR-related disorders, such as pain, ocular surface diseases, tissue damage, skin disorders, respiratory disorders and gastrointestinal disorders.

The here presented compounds are evaluated in a chronic and acute model for visceral pain as well as in a rat ocular surface disease model. In the model for visceral pain, the compounds were able to reverse the hypersensitivity status in the unhealthy model to the normal status. This effect was significantly more pronounced than a treatment with nafamostat. Nafamostat mesylate is a broad spectrum serine protease inhibitor, kallikrein inhibitor, and inhibits blood coagulation. It is also a possible complement inhibitor. In the rat ocular surface disease model, the compounds were able to significantly reverse the disease state (related to tissue damage) and showed an improved result compared towards Restasis®, which is at date of the invention the only prescription drug for dry eye treatment.

SUMMARY OF THE INVENTION

In a first aspect, the present invention provides a bis(acetamidophenyl) guanidinophenylethylphosphonate compound for use in the prevention and/or treatment of a PAR-related (protease-activated receptor) disorder selected from the list comprising: pain, ocular surface diseases, tissue damage, skin disorders, respiratory disorders, and gastrointestinal disorders.

More in particular, said bis(acetamidophenyl) guanidinophenylethylphosphonate compound for use according to this invention, is a compound of formula I

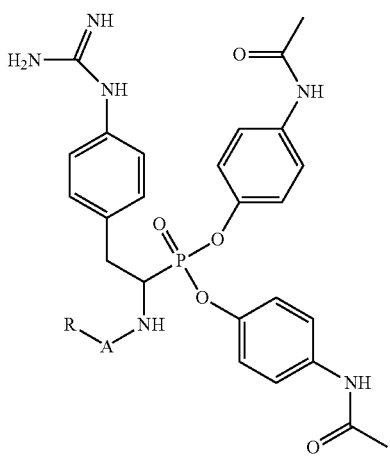

A is selected from the list comprising a direct bond, —(C=O)—, —(C=O)—O—, —(C=O)—NH—, or —SO$_2$—; and R is selected from aliphatic or aromatic groups.

In a particular embodiment of the present invention,

A is selected from the list comprising a direct bond, —(C=O)—, —(C=O)—O—, —(C=O)—NH—, or —SO$_2$—; and R is selected from —C$_{1-6}$alkyl, or a 3-6 membered aromatic cycle, wherein said —C$_{1-6}$alkyl is optionally substituted with a 3-6 membered aromatic cycle.

In a very specific embodiment, said bis(acetamidophenyl) guanidinophenylethylphosphonate compound for use according to this invention, is a compound selected from Compound 2

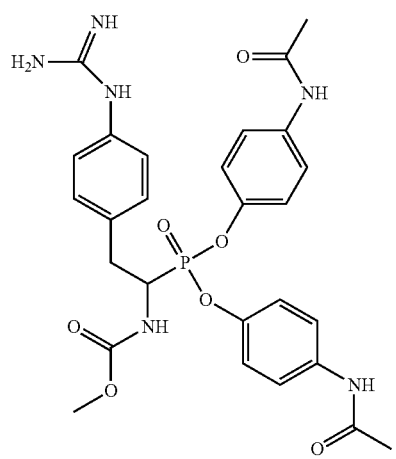

Compound 4

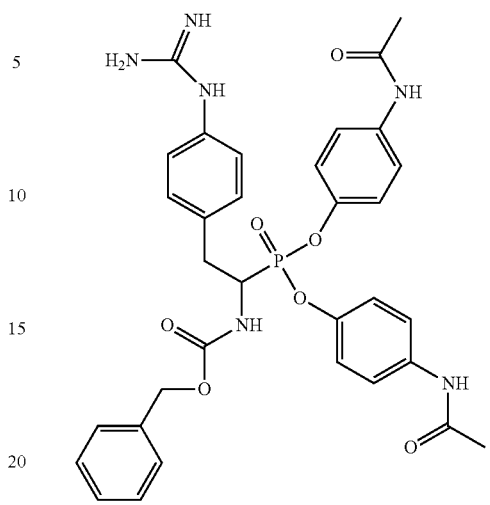

The present invention also provides a pharmaceutical composition for use in the prevention and/or treatment of a PAR-related disorder selected from the list comprising: pain, ocular surface diseases, tissue damage, skin disorders, respiratory disorders, gastrointestinal disorders; said composition comprising a bis(acetamidophenyl) guanidinophenylethylphosphonate compound as defined in anyone of claims 1 to 4.

In a particular embodiment of the present invention, the PAR-related disorder of the present invention is selected from the list comprising: pain and ocular disorders. Said pain is in particular selected from the list comprising: visceral pain, inflammatory pain, and neuropathic pain; more in particular visceral pain such as pancreatitis-related pain, postoperative pain, cancer pain, bladder pain, IBS (irritable bowel syndrome) related pain, and IBD (inflammatory bowel disease) related pain. Said ocular disorders include dry eye syndrome, meibomian gland dysfunction-blepharitis, rosaceous, allergies, scarring from glaucoma medications, chemical burns, thermal burns, and immunological conditions such as Mucous Membrane Pemphigoid and Sjogren's Syndrome and in particular selected from dry eye disease and conjunctivitis sicca; more in particular dry eye disease.

In a further aspect, the present invention provides the use of a compound or composition according to the present invention, for the prevention and/or treatment of at least one PAR-related disease selected from the list comprising: pain, ocular surface diseases, tissue damage, skin disorders, respiratory disorders, gastrointestinal disorders.

In a final aspect, the present invention provides a method for the prevention and/or treatment of at least one PAR-related disorder selected from the list comprising pain, ocular disorders, tissue damage, skin disorders, respiratory disorders, gastrointestinal disorders; said method comprising administering to a subject in need thereof a therapeutic effective amount of a compound, or a composition according to this invention.

BRIEF DESCRIPTION OF THE DRAWINGS

With specific reference now to the figures, it is stressed that the particulars shown are by way of example and for purposes of illustrative discussion of the different embodiments of the present invention only. They are presented in the cause of providing what is believed to be the most useful and readily description of the principles and conceptual aspects of the invention. In this regard no attempt is made to show structural details of the invention in more detail than is necessary for a fundamental understanding of the invention. The description taken with the drawings making apparent to those skilled in the art how the several forms of the invention may be embodied in practice.

FIG. 1 A-D: The effect of compound 4 in a post-colitis rat model for visceral pain, treating with 0.01mg/kg of compound 4 (FIG. 1A), 0.1mg/kg of compound 4 (FIG. 1B), 1 mg/kg of compound 4 (FIG. 1C), and the control model, rather than post-colitis model, treating with 1 mg/kg of compound 4 (FIG. 1D). The effect of vehicle (black symbols) and cmpd-4 on VMRs in post-colitis (square) and control (bullet) rats. Data are presented as mean±SEM. Generalized Estimating Equations (GEE)+LSD post-hoc test; n=8-11. *$p<0.05$; $p<0.01$; *$p<0.001$; significantly different from control+vehicle. #$p<0.05$; ##$p<0.01$; ###$p<0.001$; significantly different from post-colitis+vehicle.

FIG. 2 A-B: The effect of compound-1 in a post-colitis rat model for visceral pain. The effect of vehicle (black symbols) and cmpd-1 on VMRs in post-colitis (square) and control (bullet) rats. Data are presented as mean±SEM. Generalized estimating equations+LSD-post hoc test. *$p<0.05$; significantly different from 'control+vehicle'; #$p<0.05$; significantly different from 'post-colitis+vehicle'.

DETAILED DESCRIPTION OF THE INVENTION

Figure 3:
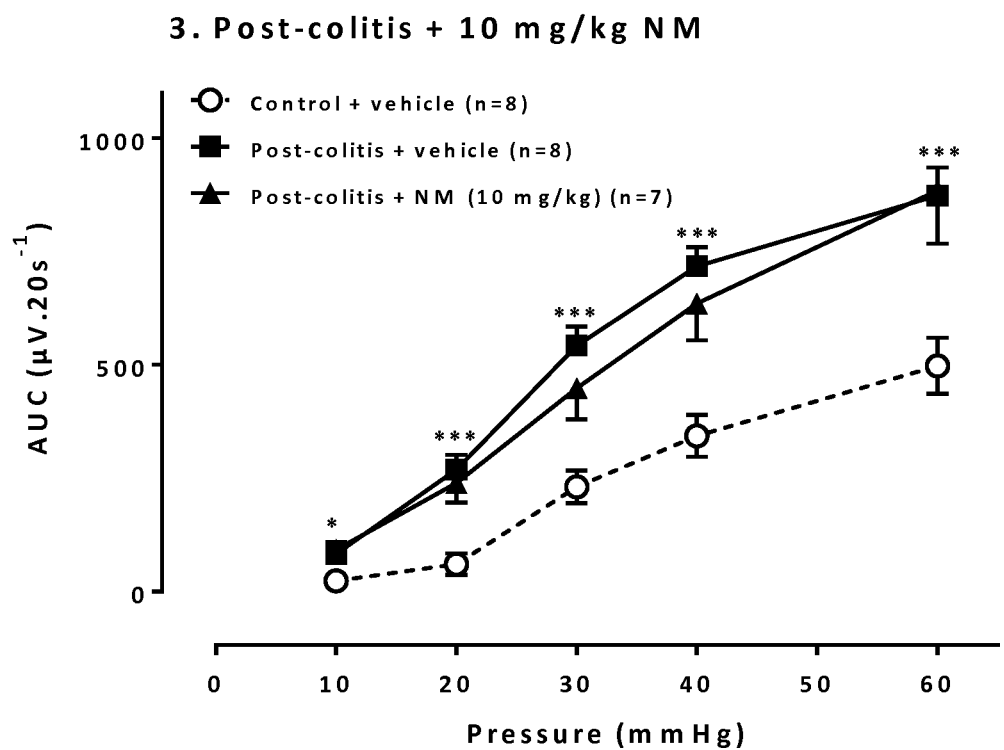
FIG. 3: The effect of nafamostat mesylate (NM) in a post-colitis rat model for visceral pain. The effect of vehicle (black symbols) and NM on VMRs in post-colitis (square) and control (bullet) rats. Data are presented as mean±SEM. Generalized Estimating Equations (GEE)+LSD post-hoc test; n=7-8. *$p<0.05$; $p<0.01$; *$p<0.001$; significantly different from control+vehicle.

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

As already indicated herein before, in a first aspect, the present invention provides a bis(acetamidophenyl) guanidinophenylethylphosphonate compound for use in the prevention and/or treatment of a PAR-related (protease-activated receptor) disorder selected from the list comprising: pain, ocular surface diseases, tissue damage, skin disorders, respiratory disorders, gastrointestinal disorders.

It is known that serine proteases are involved in ocular surface diseases and visceral pain or hypersensitivity but until now, no optimal small molecule serine protease inhibitors are presented to treat pain or ocular surface diseases (e.g. dry eye). This is probably due to the fact that these disorders are PAR-related disorders and that several trypsine-like serine proteases such as kallikreins, trypsin, tryptase, thrombin, cathepsinG, matriptase and uPA are known to activate the Protease activated receptors (PAR).

Protease activated receptors are a subfamily of related G protein-coupled receptors that are activated by cleavage of part of their extracellular domain. There are 4 known protease-activated receptors or PARs, i.e. PAR1, PAR2, PAR3 and PAR4. In the context of the present invention, each of these PARs is intended with the more general term PAR, however, in particular the invention relates to PAR2 or PAR4; more in particular PAR2.

Hence, in a specific embodiment, the present invention relates to bis(acetamidophenyl) guanidinophenylethylphosphonate compound for use in the prevention and/or treatment of a PAR1-, PAR2-, PAR3- or PAR4-related disorder selected from the list comprising: pain, ocular surface diseases, tissue damage, skin disorders, respiratory disorders, gastrointestinal disorders.

More specifically the present invention relates to bis (acetamidophenyl) guanidinophenylethylphosphonate compound for use in the prevention and/or treatment of a PAR2-related disorder selected from the list comprising: pain, ocular surface diseases, tissue damage, skin disorders, respiratory disorders, gastrointestinal disorders.

It should be noted that the present invention also relates to bis(acetamidophenyl) guanidinophenylethylphosphonate compound for use in the prevention and/or treatment of a disorder selected from the list comprising: pain, ocular surface diseases, tissue damage, skin disorders, respiratory disorders, gastrointestinal disorders; more in particular pancreatitis-related pain, postoperative pain, cancer pain, bladder pain, IBS (irritable bowel syndrome) pain, IBD (inflammatory bowel disease) pain, dry eye syndrome, meibomian gland dysfunction blepharitis, rosaceous, allergies, scarring from glaucoma medications, chemical burns, thermal burns, and immunological conditions such as Mucous Membrane Pemphigoid and Sjogren's Syndrome.

Most serine protease inhibitors tested in visceral pain or visceral hypersensitivity have a too aspecific profile to be developed as a therapy or are too specific and have not the full potential to stop PAR activation.

Also recently, endogenous serine protease inhibitors such as SERPINA3K were presented as a possible solution to treat dry eye (Lin et al., 2014; Hu et al., 2013), however, the physicochemical and chemical properties of such compounds hamper their fast development towards a pharmaceutical drug. Moreover, not just any serine protease inhibitor can be presented as a possible treatment strategy.

We have found that even very closely relating analogues such diphenyl guanidinophenylethylphosphonates and bis (acetamidophenyl) guanidinophenylethylphosphonates seem to show a significantly different impact in an in vivo model for visceral hypersensitivity as well as in an in vivo model for ocular surface disease. Diphenyl guanidinophenylethylphosphonates and bis(acetamidophenyl) guanidinophenylethylphosphonates were described as selective uPA inhibitors with potent anti-metastatic properties in an in vivo cancer model (WO2007045496). Diphenyl phosphonates are the standard template to start the design and synthesis for irreversible serine protease inhibitors. Most synthetic programs around the aryl phosphonate template start with a diphenyl phosphonate warhead due to the easy synthetic protocol to generate analogues. The selectivity profile of this type of compounds is modified by incorporating different chemical building blocks or peptidic tails.

Most people skilled in the art aim to design very potent and selective serine protease inhibitors. However, we identified here for the first time that a well-defined multi-target inhibition profile of the here disclosed inhibitors was beneficial to obtain an in vivo effect in a visceral pain model as well as in an ocular surface disease model. Pronounced differences in the selectivity profile of very close analogues such as Diphenyl guanidinophenylethylphosphonates and bis(acetamidophenyl) guanidinophenylethylphosphonates were identified. The fact that bis(acetamidophenyl) guanidinophenylethylphosphonates showed a less selective profile to matriptase, cathepsinG and tryptase would have moved a person skilled in the art away from these chemical series, however we identified this aspecific profile as an opportunity in the treatment of PAR-related disorders, such as visceral pain or visceral hypersensitivity diseases and ocular surface diseases, and moved these compounds forward towards in vivo evaluation.

As far as we know no combined potent inhibition of uPA, matriptase, tryptase and cathepsinG is ever reported for bis(acetamidophenyl) guanidinophenylethylphosphonates compounds. Surprisingly these bis(acetamidophenyl) guanidinophenylethylphosphonates compounds showed a more pronounced effect in a model for chronic visceral pain and in an ocular surface disease model, compared to the more selective diphenyl guanidinophenylethylphosphonate inhibitors and to a broad spectrum serine protease inhibitor such as nafamostat in the chronic visceral pain model.

We confirm here that an optimal multi-target serine inhibition profile and physicochemical properties are necessary to have this pronounced effect on inhibition of PAR activation. It is however important for further drug development aspects that the impact on serine proteases involved in the blood coagulation and fibrinolytic cascade is manageable. Most aspecific serine protease inhibitors show also a very strong interaction with enzymes such e.g. plasmine, tPA and FXIIa and thrombin or on proteases that have a protective function. Based on the in vivo results it seems that we have found the right inhibitory balance to have a positive impact on the hypersensitivity.

In a particular embodiment, the present invention provides a bis(acetamidophenyl) guanidinophenylethylphosphonate compound for use in the prevention and/or treatment of a PAR-related (protease-activated receptor) disorder selected from the list comprising: pain, ocular surface disease, tissue damage, skin disorders, respiratory disorders, gastrointestinal disorders, wherein said compound is a compound of formula I

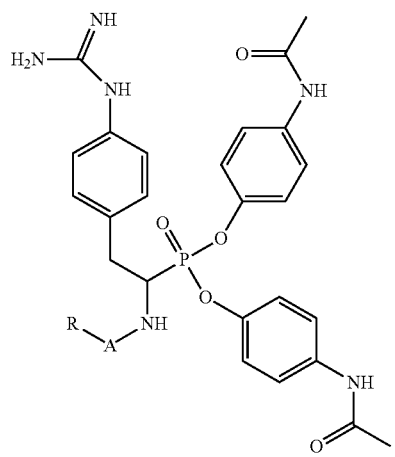

wherein
A is selected from the list comprising a direct bond, —(C═O)—, —(C═O)—O—, —(C═O)—NH—, or —SO$_2$—; and
R is selected from aliphatic or aromatic groups.

In another particular embodiment, the present invention provides a bis(acetamidophenyl) guanidinophenylethylphosphonate compound for use in the prevention and/or treatment of a PAR-related disorder selected from the list comprising: pain, ocular surface disease, tissue damage, skin disorders, respiratory disorders, gastrointestinal disorders, is a compound of formula I wherein
A is selected from the list comprising a direct bond, —(C═O)—, —(C═O)—O— or —(C═O)—NH—, —SO$_2$—; and
R is selected from —C$_{1-6}$alkyl, or a 3-6 membered aromatic cycle, wherein said —C$_{1-6}$alkyl is optionally substituted with a 3-6 membered aromatic cycle.

In another particular embodiment, the present invention provides a bis(acetamidophenyl) guanidinophenylethylphosphonate compound for use in the prevention and/or treatment of a PAR-related disorder selected from the list comprising: pain, ocular surface disease, tissue damage, skin disorders, respiratory disorders, gastrointestinal disorders, is a compound of formula I
wherein
A is —(C═O)—O—; and
R is selected from —C$_{1-6}$alkyl, or a 3-6 membered aromatic cycle, wherein said —C$_{1-6}$alkyl is optionally substituted with a 3-6 membered aromatic cycle.

In yet a further embodiment, the present invention provides a bis(acetamidophenyl) guanidinophenylethylphosphonate compound for use in the prevention and/or treatment of a PAR-related disorder selected from the list comprising: pain, ocular surface disease, tissue damage, skin disorders, respiratory disorders, gastrointestinal disorders, is a compound of formula I
wherein
A is —(C═O)—O—; and
R is selected from —C$_{1-6}$alkyl, or —C$_{1-6}$alkyl substituted with a 3-6 membered aromatic cycle.

In yet a further embodiment, the present invention provides a bis(acetamidophenyl) guanidinophenylethylphosphonate compound for use in the prevention and/or treatment of a PAR-related disorder selected from the list comprising: pain, ocular surface disease, tissue damage, skin disorders, respiratory disorders, gastrointestinal disorders, is a compound of formula I, wherein
A is —(C=O)—O—; and
R is selected from -methyl, optionally substituted with -phenyl.

When describing the compounds of the invention, the terms used are to be construed in accordance with the following definitions, unless a context dictates otherwise:

Unless a context dictates otherwise, asterisks are used herein to indicate the point at which a mono- or bivalent radical depicted is connected to the structure to which it relates and of which the radical forms part. In that respect A is preferably selected from the list comprising: *—(C=O)—, *—(C=O)—O—, *—(C=O)—NH—, or *—SO$_2$—; wherein the asterisk indicates the attachment point of said group to the structure represented by formula I.

The term "aliphatic groups" is meant to include any non-aromatic organic group, which can be saturated or non-saturated and which includes both straight and branched chains as well as cyclic compounds. Aliphatic groups in particular encompass alkanes, alkenes and alkynes. An aliphatic group may consists purely of C and H atoms, but it may also contain heteroatoms such as N, O or S; or halogen atoms such as F, Cl, . . . . In the context of the present invention, the aliphatic group may for example be —C$_{1-6}$alkyl.

The term "alkyl" by itself or as part of another substituent refers to a fully saturated hydrocarbon of Formula C$_x$H$_{2x+1}$ wherein x is a number greater than or equal to 1. Generally, alkyl groups of this invention comprise from 1 to 20 carbon atoms. Alkyl groups may be linear or branched and may be substituted as indicated herein. When a subscript is used herein following a carbon atom, the subscript refers to the number of carbon atoms that the named group may contain. Thus, for example, C$_{1-4}$alkyl means an alkyl of one to four carbon atoms. Examples of alkyl groups are methyl, ethyl, n-propyl, i-propyl, butyl, and its isomers (e.g. n-butyl, i-butyl and t-butyl); pentyl and its isomers, hexyl and its isomers, heptyl and its isomers, octyl and its isomers, nonyl and its isomers; decyl and its isomers. C$_1$-C$_6$ alkyl includes all linear, branched, or cyclic alkyl groups with between 1 and 6 carbon atoms, and thus includes methyl, ethyl, n-propyl, i-propyl, butyl and its isomers (e.g. n-butyl, i-butyl and t-butyl); pentyl and its isomers, hexyl and its isomers, cyclopentyl, 2-, 3-, or 4-methylcyclopentyl, cyclopentylmethylene, and cyclohexyl.

The term "optionally substituted alkyl" refers to an alkyl group optionally substituted with one or more substituents (for example 1 to 4 substituents, for example 1, 2, 3, or 4 substituents or 1 to 2 substituents) at any available point of attachment. Non-limiting examples of such substituents include halo, hydroxyl, carbonyl, nitro, amino, oxime, imino, azido, hydrazino, cyano, aryl, heteroaryl, cycloalkyl, acyl, alkylamino, alkoxy, thiol, alkylthio, carboxylic acid, acylamino, alkyl esters, carbamate, thioamido, urea, sulfonamido and the like.

The term "alkene", as used herein, unless otherwise indicated, means straight-chain, cyclic, or branched-chain hydrocarbon radicals containing at least one carbon-carbon double bond. Examples of alkenyl radicals include ethenyl, E- and Z-propenyl, isopropenyl, E- and Z-butenyl, E- and Z-isobutenyl, E- and Z-pentenyl, E- and Z-hexenyl, E,E-, E,Z-, Z,E-, Z,Z-hexadienyl, and the like. An optionally substituted alkenyl refers to an alkenyl having optionally one or more substituents (for example 1, 2, 3 or 4), selected from those defined above for substituted alkyl.

The term "alkyne", as used herein, unless otherwise indicated, means straight-chain or branched-chain hydrocarbon radicals containing at least one carbon-carbon triple bond. Examples of alkynyl radicals include ethynyl, E- and Z-propynyl, isopropynyl, E- and Z-butynyl, E- and Z-isobutynyl, E- and Z-pentynyl, E, Z-hexynyl, and the like. An optionally substituted alkynyl refers to an alkynyl having optionally one or more substituents (for example 1, 2, 3 or 4), selected from those defined above for substituted alkyl.

Where alkyl groups as defined are divalent, i.e., with two single bonds for attachment to two other groups, they are termed "alkylene" groups. Non-limiting examples of alkylene groups includes methylene, ethylene, methylmethylene, trimethylene, propylene, tetramethylene, ethylethylene, 1,2-dimethylethylene, pentamethylene and hexamethylene. Similarly, where alkenyl groups as defined above and alkynyl groups as defined above, respectively, are divalent radicals having single bonds for attachment to two other groups, they are termed "alkenylene" and "alkynylene" respectively.

Generally, alkylene groups of this invention preferably comprise the same number of carbon atoms as their alkyl counterparts. Where an alkylene or cycloalkylene biradical is present, connectivity to the molecular structure of which it forms part may be through a common carbon atom or different carbon atom, preferably a common carbon atom. To illustrate this applying the asterisk nomenclature of this invention, a C$_3$ alkylene group may be for example *—CH$_2$CH$_2$CH$_2$—*, *—CH(—CH$_2$CH$_3$)—*, or *—CH$_2$CH(—CH$_3$)—*. Likewise a C$_3$ cycloalkylene group may be

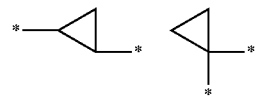

The term "aromatic group" is meant to include "aryl" which refers to a polyunsaturated, aromatic hydrocarbyl group having a single ring (i.e. phenyl) or multiple aromatic rings fused together (e.g. naphthalene or anthracene) or linked covalently, typically containing 6 to 10 atoms; wherein at least one ring is aromatic. The aromatic ring may optionally include one to three additional rings (either cycloalkyl, heterocyclyl, or heteroaryl) fused thereto. Aryl is also intended to include the partially hydrogenated derivatives of the carbocyclic systems enumerated herein. Non-limiting examples of aryl comprise phenyl, biphenylyl, biphenylenyl, 5- or 6-tetralinyl, 1-, 2-, 3-, 4-, 5-, 6-, 7-, or 8-azulenyl, 1- or 2-naphthyl, 1-, 2-, or 3-indenyl, 1-, 2-, or 9-anthryl, 1- 2-, 3-, 4-, or 5-acenaphtylenyl, 3-, 4-, or 5-acenaphtenyl, 1-, 2-, 3-, 4-, or 10-phenanthryl, 1- or 2-pentalenyl, 1, 2-, 3-, or 4-fluorenyl, 4- or 5-indanyl, 5-, 6-, 7-, or 8-tetrahydronaphthyl, 1,2,3,4-tetrahydronaphthyl, 1,4-dihydronaphthyl, dibenzo[a,d]cylcoheptenyl, and 1-, 2-, 3-, 4-, or 5-pyrenyl.

The aryl ring can optionally be substituted by one or more substituents. An "optionally substituted aryl" refers to an aryl having optionally one or more substituents (for example 1 to 5 substituents, for example 1, 2, 3 or 4) at any available point of attachment. Non-limiting examples of such substituents are selected from halogen, hydroxyl, oxo, nitro, amino, hydrazine, aminocarbonyl, azido, cyano, alkyl, cycloalkyl, alkenyl, alkynyl, cycloalkylalkyl, alkylamino, alkoxy, —SO$_2$—NH$_2$, aryl, heteroaryl, aralkyl, haloalkyl, haloalkoxy, alkoxycarbonyl, alkylaminocarbonyl, heteroarylalkyl, alkylsulfonamide, heterocyclyl, alkylcarbonylaminoalkyl, aryloxy, alkylcarbonyl, acyl, arylcarbonyl, aminocarbonyl, alkylsulfoxide, —SO$_2$R$^a$, alkylthio, carboxyl, and the like, wherein R$^a$ is alkyl or cycloalkyl.

Where a carbon atom in an aryl group is replaced with a heteroatom, the resultant ring is referred to herein as a heteroaryl ring.

The term "carboxy" or "carboxyl" or "hydroxycarbonyl" by itself or as part of another substituent refers to the group —CO$_2$H. Thus, a carboxyalkyl is an alkyl group as defined above having at least one substituent that is —CO$_2$H.

The term "alkoxycarbonyl" by itself or as part of another substituent refers to a carboxy group linked to an alkyl radical i.e. to form —C(=O)OR$^e$, wherein R$^e$ is as defined above for alkyl. The term "halo" or "halogen" as a group or part of a group is generic for fluoro, chloro, bromo, or iodo.

Whenever the term "substituted" is used in the present invention, it is meant to indicate that one or more hydrogens on the atom indicated in the expression using "substituted" is replaced with a selection from the indicated group, provided that the indicated atom's normal valency is not exceeded, and that the substitution results in a chemically stable compound, i.e. a compound that is sufficiently robust to survive isolation to a useful degree of purity from a reaction mixture, and formulation into a therapeutic agent.

Where groups may be optionally substituted, such groups may be substituted with one or more, and preferably once, twice or thrice.

As used herein the terms such as "alkyl, aryl, or cycloalkyl, each being optionally substituted with" or "alkyl, aryl, or cycloalkyl, optionally substituted with" refers to optionally substituted alkyl, optionally substituted aryl and optionally substituted cycloalkyl.

More generally, from the above, it will be clear to the skilled person that the compounds of the invention may exist in the form of different isomers and/or tautomers, including but not limited to geometrical isomers, conformational isomers, E/Z-isomers, stereochemical isomers (i.e. enantiomers and diastereoisomers) and isomers that correspond to the presence of the same substituents on different positions of the rings present in the compounds of the invention. All such possible isomers, tautomers, racemics and mixtures thereof are included within the scope of the invention.

Whenever used in the present invention the term "compounds of the invention" or a similar term is meant to include the compounds of general Formula I and any subgroup thereof. This term also refers to their derivatives, N-oxides, salts, solvates, hydrates, stereoisomeric forms, racemic mixtures, tautomeric forms, optical isomers, analogues, pro-or-predrugs, esters, and metabolites, as well as their quaternized nitrogen analogues. The N-oxide forms of said compounds are meant to comprise compounds wherein one or several nitrogen atoms are oxidized to the so-called N-oxide.

As used in the specification and the appended claims, the singular forms "a", "an", and "the" include plural referents unless the context clearly dictates otherwise. By way of example, "a compound" means one compound or more than one compound.

The terms described above and others used in the specification are well understood to those in the art.

In a very specific embodiment, the present invention provides a compound selected from the list comprising:

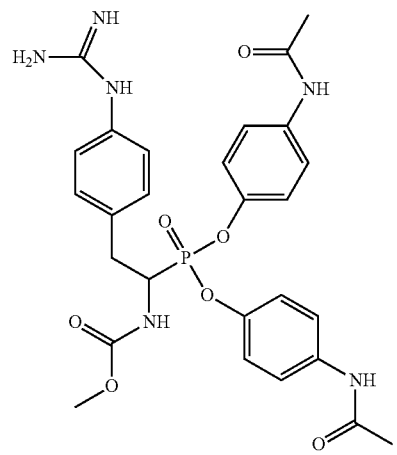

Compound 2

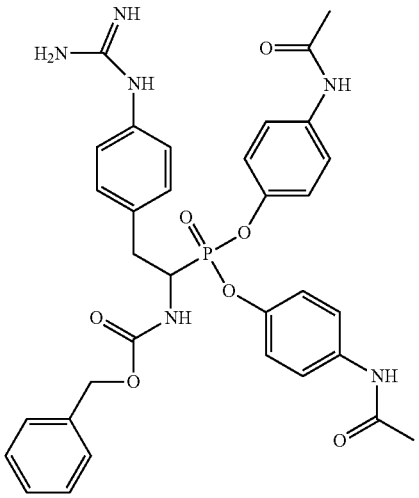

Compound 4 for use in the prevention and/or treatment of a PAR-related disorder selected from the list comprising: pain, ocular surface diseases, tissue damage, skin disorders, respiratory disorders, gastrointestinal disorders.

The present invention also provides a pharmaceutical composition for use in the prevention and/or treatment of a PAR-related disorder selected from the list comprising: pain, ocular surface diseases, tissue damage, skin disorders, respiratory disorders, gastrointestinal disorders; said composition comprising a bis(acetamidophenyl) guanidinophenylethylphosphonate compound as defined in anyone of claims 1 to 4.

It is evident for a person skilled in the art, that the compositions according to the present invention may further comprise additional active ingredients which are suitable for use in the treatment of the PAR-related disorders according to this invention.

In a particular embodiment of the present invention, the PAR-related disorder of the present invention is selected from the list comprising: pain and ocular surface diseases. Said pain is in particular selected from the list comprising: visceral pain, inflammatory pain, and neuropathic pain; more in particular visceral pain such as pancreatitis-related pain, postoperative pain, cancer pain, bladder pain, IBS (irritable bowel syndrome) pain, and IBD (inflammatory bowel disease) pain. Said ocular disorders include dry eye syndrome, meibomian gland dysfunctionblepharitis, rosaceous, allergies, scarring from glaucoma medications, chemical burns, thermal burns, and immunological conditions such as Mucous Membrane Pemphigoid and Sjogren's Syndrome and are in particular selected from dry eye disease and conjunctivitis sicca; more in particular dry eye disease.

The compounds of the present invention can be prepared according to the reaction schemes provided in WO2014140299, as further detailed in the examples hereinafter, but those skilled in the art will appreciate that these are only illustrative for the invention and that the compounds of this invention can be prepared by any of several standard synthetic processes commonly used by those skilled in the art of organic chemistry.

In a further aspect, the invention provides the use of a compound as defined hereinbefore or the use of a composition comprising said compound in the prevention and/or treatment of at least one PAR-related disease selected from the list comprising: pain hypersensitivity, ocular surface diseases, tissue damage, skin disorders, respiratory disorders, gastrointestinal disorders.

Method of Treatment

The present invention further provides a method for the prevention and/or treatment of at least one PAR-related disease or disorder selected from the group comprising pain, ocular surface diseases, tissue damage, skin disorders, respiratory disorders, gastrointestinal disorders; said method comprising administering to a subject in need thereof a therapeutic effective amount of a compound, or a composition according to this invention. More specifically, the present invention provides a method for the prevention and/or treatment of at least one PAR-related disease or disorder selected from the group comprising pancreatitis-related pain, postoperative pain, cancer pain, bladder pain, IBS (irritable bowel syndrome) pain, IBD (inflammatory bowel disease) pain, dry eye syndrome, meibomian gland dysfunction blepharitis, rosaceous, allergies, scarring from glaucoma medications, chemical burns, thermal burns, and immunological conditions such as Mucous Membrane Pemphigoid and Sjogren's Syndrome; said method comprising administering to a subject in need thereof a therapeutic effective amount of a compound, or a composition according to this invention.

In the invention, particular preference is given to compounds of Formula I or any subgroup thereof that in the inhibition assay for described below inhibit with an $IC_{50}$ value of less than 500 nM µM, preferably less than 100 nM and most optimal less than 10 nM. At least matriptase and tryptase are involved in the inhibitory profile, this profile can be extended by but not limited to tissue kallikreins (e.g. KLK2, KLK4, KLK14), cathepsin G, uPA and trypsin.

Said inhibition may be effected in vitro and/or in vivo, and when effected in vivo, is preferably effected in a multi-target manner, as defined above.

For pharmaceutical use, the compounds of the invention may be used as a free acid or base, and/or in the form of a pharmaceutically acceptable acid-addition and/or base-addition salt (e.g. obtained with non-toxic organic or inorganic acid or base), in the form of a hydrate, solvate and/or complex, and/or in the form or a pro-drug or pre-drug, such as an ester. As used herein and unless otherwise stated, the term "solvate" includes any combination which may be formed by a compound of this invention with a suitable inorganic solvent (e.g. hydrates) or organic solvent, such as but not limited to alcohols, ketones, esters and the like. Such salts, hydrates, solvates, etc. and the preparation thereof will be clear to the skilled person; reference is for instance made to the salts, hydrates, solvates, etc. described in U.S. Pat. Nos. 6,372,778, 6,369,086, 6,369,087 and 6,372,733.

The pharmaceutically acceptable salts of the compounds according to the invention, i.e. in the form of water-, oil-soluble, or dispersible products, include the conventional non-toxic salts or the quaternary ammonium salts which are formed, e.g., from inorganic or organic acids or bases. Generally, for pharmaceutical use, the compounds of the inventions may be formulated as a pharmaceutical preparation or pharmaceutical composition comprising at least one compound of the invention and at least one pharmaceutically acceptable carrier, diluent or excipient and/or adjuvant, and optionally one or more further pharmaceutically active compounds.

By means of non-limiting examples, such a formulation may be in a form suitable for oral administration, for parenteral administration (such as by intravenous, intramuscular or subcutaneous injection or intravenous infusion), for topical administration (including ocular), for administration by inhalation, by a skin patch, by an implant, by a suppository, etc. Such suitable administration forms—which may be solid, semi-solid or liquid, depending on the manner of administration—as well as methods and carriers, diluents and excipients for use in the preparation thereof, will be clear to the skilled person; reference is again made to for instance U.S. Pat. Nos. 6,372,778, 6,369,086, 6,369,087 and 6,372,733, as well as to the standard handbooks, such as the latest edition of Remington's Pharmaceutical Sciences.

The compounds may be formulated with carriers, excipients, and diluents that are suitable per se for such formulations. The formulations can optionally contain other pharmaceutically active substances (which may or may not lead to a synergistic effect with the compounds of the invention) and other substances that are commonly used in pharmaceutical formulations, such as lubricating agents, wetting agents, emulsifying and suspending agents, dispersing agents, desintegrants, bulking agents, fillers, preserving agents, sweetening agents, flavoring agents, flow regulators, release agents, etc. The compositions may also be formulated so as to provide rapid, sustained or delayed release of the active compound(s) contained therein.

In addition, co-solvents such as alcohols may improve the solubility and/or the stability of the compounds. In the preparation of aqueous compositions, addition of salts of the compounds of the invention can be more suitable due to their increased water solubility.

The preparations may be prepared in a manner known per se, which usually involves mixing at least one compound according to the invention with the one or more pharmaceutically acceptable carriers, and, if desired, in combination with other pharmaceutical active compounds, when necessary under aseptic conditions. Reference is again made to U.S. Pat. Nos. 6,372,778, 6,369,086, 6,369,087 and 6,372,733 and the further prior art mentioned above, as well as to the standard handbooks, such as the latest edition of Remington's Pharmaceutical Sciences.

The pharmaceutical preparations of the invention are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 1 and 1000 mg, and usually between 5 and 500 mg, of the at least one compound of the invention, e.g. about 10, 25, 50, 100, 200, 300 or 400 mg per unit dosage.

The compounds can be administered by a variety of routes including the oral, rectal, ocular, transdermal, subcutaneous, intravenous, intramuscular or intranasal routes, depending mainly on the specific preparation used and the condition to be treated or prevented, and with oral and intravenous administration usually being preferred. The at least one compound of the invention will generally be administered in an "effective amount", by which is meant any amount of a compound of the Formula I, II or III or any subgroup thereof that, upon suitable administration, is sufficient to achieve the desired therapeutic or prophylactic effect in the individual to which it is administered. The amount(s) to be administered, the route of administration and the further treatment regimen may be determined by the treating clinician, depending on factors such as the age, gender and general condition of the patient and the nature and severity of the disease/symptoms to be treated. Reference is again made to U.S. Pat. Nos. 6,372,778, 6,369,086, 6,369,087 and 6,372,733 and the further prior art mentioned above, as well as to the standard handbooks, such as the latest edition of Remington's Pharmaceutical Sciences.

In accordance with the method of the present invention, said pharmaceutical composition can be administered separately at different times during the course of therapy or concurrently in divided or single combination forms. The present invention is therefore to be understood as embracing all such regimes of simultaneous or alternating treatment and the term "administering" is to be interpreted accordingly.

The compositions are of value in the veterinary field, which for the purposes herein not only includes the prevention and/or treatment of diseases in animals, but also—for economically important animals such as cattle, pigs, sheep, chicken, fish, etc.—enhancing the growth and/or weight of the animal and/or the amount and/or the quality of the meat or other products obtained from the animal. Thus, in a further aspect, the invention relates to a composition for veterinary use that contains at least one compound of the invention and at least one suitable carrier (i.e. a carrier suitable for veterinary use). The invention also relates to the use of a compound of the invention in the preparation of such a composition.

The invention will now be illustrated by means of the following synthetic and biological examples, which do not limit the scope of the invention in any way.

EXAMPLES

Example 1: Compound Synthesis & Physicochemical Properties

The compounds of the present invention may be prepared in accordance with the synthesis routes as described in WO2007045496. In particular, compound 4 of the present invention corresponds to compound 9b of WO2007045496; compound 2 of the present invention corresponds to compound 35b of WO2007045496. Also detailed information with respect to their physicochemical properties can be found in WO2007045496.

Example 2: In Vitro Assays

Overview of the Biochemical Profile

Table 1 shows that compounds 2 and 4 (bis(acetamidophenyl) guanidinophenylethylphosphonates) are more potent matriptase, tryptase and cathepsinG inhibitors than compounds 1 and 3 (diphenyl guanidinophenylethylphosphonates). All these enzymes are known to activate the PAR2 receptor.

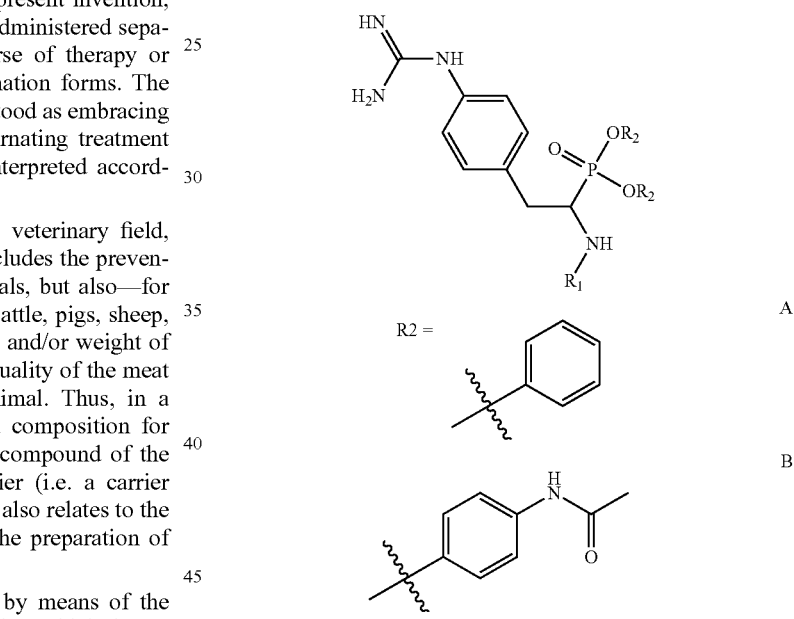

TABLE 1

Comparison of in vitro profiles

IC50 values (in µM)

| Structure | Nafamostat | $R_1 =$ —O | $R_1 =$ (benzyl) | | |
|---|---|---|---|---|---|
| Target | | $R_2 = A$ | $R_2 = B$ | $R_2 = A$ | $R_2 = B$ |
| Compound No | Ref. Cmp | Ref Cmp No 1 | Cmp No 2 | Ref Cmp No 3 | Cmp No 4 |
| uPA | <0.001 | 0.004 | 0.003 | 0.007 | 0.002 |
| tPA | >2.5 | >2.5 | >2.5 | >2.5 | >2.5 |
| thrombin | ≈500 | >2.5 | 2.5 | 2.5 | 0.257 |
| plasmin | ≈0.050 | >2.5 | >2.5 | >2.5 | >2.5 |

TABLE 1-continued

Comparison of in vitro profiles

IC50 values (in µM)

| Structure | Nafamostat | $R_1 = $ -O-C(=O)- (methyl ester) | | $R_1 = $ -CH$_2$-C$_6$H$_5$-O-C(=O)- (benzyl ester) | |
| --- | --- | --- | --- | --- | --- |
| tryptase | <0.001 | 0.093 | 0.003 | 0.083 | 0.005 |
| cathepsinG | ND | 0.329 | 0.061 | ND | 0.120 |
| matriptase | <0.001 | 0.082 | 0.008 | 0.150 | 0.003 |
| KLK1 | ≈1 | >2.5 | >2.5 | >2.5 | >2.5 |
| KLK2 | ≈0.10 | >2.5 | 0.315 | 0.090 | 0.115 |
| KLK4 | ND | 0.009 | 0.026 | 0.012 | 0.002 |
| KLK8 | ≈0.015 | 0.028 | 0.013 | 0.042 | 0.002 |
| FXIIa | ND | >2.5 | 3.14 | ND | 1.61 |
| HNE | >2.5 | >2.5 | >2.5 | >2.5 | >2.5 |

Example 3: In Vivo Assays—Visceral Pain

Materials and Methods

Animals

Male Sprague-Dawley rats (200-225 g; Charles River, Italy) were used in all experiments. Rats were housed at a constant room temperature (22±2° C.) and humidity (60%). The animals had unlimited access to water and food and were kept on a 12 h:12 h day-night cycle. They were allowed to acclimatize for at least 1 week before the start of the experiments. All experiments were approved by the Ethical Committee for Animal Experiments of the University of Antwerp (EC nr. 2014-41).

Experimental Design

In this set-up, a mild colitis was induced in the post-colitis group on day 0, using a TNBS-enema. The control group received an intrarectal administration with 0.9% NaCl. The presence of colitis was verified by a colonoscopy on day 3. From day 10 onwards, a colonoscopy was performed every 4 days to follow-up the healing of the colonic mucosa. When the colonic mucosa was completely healed, further experiments were performed 3 days later. An active compound or vehicle was injected intraperitoneally (i.p.) 30 minutes before the start of the visceromotor response (VMR) experiment. After the VMR measurement, the animals were sacrificed.

Induction of TNBS-Colitis

TNBS-colitis was induced at day 0 using a TNBS-enema (4 mg TNBS, 50% ethanol). After an overnight fast, 0.25 ml of the TNBS-enema was administered intrarectally using a flexible catheter (18G, length 4.5 cm), under pentobarbital anesthesia (45 mg/kg, i.p.). Control animals received 0.25 ml 0.9% NaCl intrarectally. The animals were kept in a tail-up position during 1 min and were then allowed to recover in a Trendelenburg position.

Visceromotor Response

The visceromotor response (VMR) can be defined as a nociceptive reflex with a contraction of the abdominal muscles in response to a colorectal balloon distension (Ness et al. 1988). The VMR is a validated, objective method, frequently used in our lab, to quantify the visceral sensitivity (Vermeulen et al. 2013, Deiteren et al. 2014, Deiteren et al. 2015). Electromyographic (EMG) electrodes were implanted into the external abdominal muscle and 3 days later, the VMR experiment was performed in conscious rats. A lubricated balloon (length 5 cm) was introduced into the colorectum of the animal and connected to a barostat (Distender Series II Barostat, G&J Electronics, Canada). The EMG electrodes were attached to a data-acquisition system and a phasic distension protocol (10-20-30-40-60 mmHg, 20 s, 4 min interval) was sent through the barostat. The EMG signal was registered, amplified (Neurolog, Digitimer Ltd, UK) and digitalized (CED 1401, Cambridge Electronic Design, UK) and the EMG recordings were analyzed using Spike2 V.5.16 (Cambridge Electronic Design, UK). The VMR was quantified using the area under the curve (AUC) of the EMG signal during the distension (20 s) corrected for the EMG signal before the distension (20 s).

Statistical Analysis

All data are presented as mean±SEM. The statistical analysis was performed using SPSS 22.0. The results of the VMR experiments analyzed using a Generalized Estimating Equations (GEE) test with Least Significant Difference (LSD) post-hoc test. A p-value<0.05 was considered as being statistically significant. The graphs were made with GraphPad Prism 6.0.

Results

Overview of the In Vivo Comparison Between Compound 1 and 4.

In these experiments, a validated post-colitis rat model for visceral pain was used (Deiteren et al., 2014). Visceral sensitivity was assessed using the visceromotor responses (VMRs) to a colorectal distension, shown in the graphs below as area under the curve (AUC; y-axis; µV. 20s-1) for each distension pressure (x-axis; mmHg). Serine proteases seem to play an important role in the pathogenesis of visceral pain. We studied the effect of two newly developed serine protease inhibitors (compound-1 and compound-4) with a nearly comparable chemical structure but with a distinct difference in biochemical inhibition profile on the serine proteases tryptase, cathepsinG and matriptase and we used nafamostat mesylate (a serine protease inhibitor marketed in Japan) as a broad spectrum trypsin-like serine protease inhibitor.

The vehicle-treated post-colitis rats showed higher VMRs, indicating the presence of visceral pain (FIG. 1A). A single administration with cmpd-4 reduced visceral pain in a dose-dependent manner. In a dose of 0.01 mg/kg, cmpd-4 had no significant effect, whereas 0.1 mg/kg already significantly lowered VMRs and after the administration of 1 mg/kg cmpd-4, visceral pain had completely disappeared (FIG. 1A-C). In control animals, cmpd-4 had no significant effect on visceral sensitivity in a dose of 1 mg/kg (FIG. 1D). For compound 1, a dose-dependent effect seems to be present: in a dose of 1 mg/kg, no clear reduction of the VMRs was seen, however in a dose of 2.5 mg/kg visceral pain had completely disappeared (FIG. 2A-B). This compound however, shows some disadvantages compared to cmpd-4: first of all in a dose of 5 mg/kg, sedation was observed in these animals and secondly, a lower inhibitory activity seems to be present as a higher dose is needed to observe the same effects compared to cmpd-4. Finally, nafamostat mesylate was tested in our model in a dose of 10 mg/kg, but no significant effect on visceral pain could be detected (FIG. 3).

From these experiments it can be concluded that compound 4 seems to be the most effective and beneficial for the indication of visceral pain. Compound 4 is effective at 0.1 mg/kg which leads to sufficient safety margin, whereas compound 1 is only significant active at a dose of at least 2.5 mg/kg, and showed side effects at a 5 mg/kg dose. The difference in therapeutic activity can be explained by the similar difference in potency between the $IC_{50}$ values on matriptase, tryptase and cathepsin G. Based on this correlation we can state that compound 2 will probably also show the same therapeutic effect.

Interestingly, the broad spectrum serine protease inhibitor nafamostat didn't show any therapeutic effect at 10 mg/kg dose. This indicates that the bis(acetamidophenyl) guanidinophenylethylphosphonates have unexpected biochemical and physicochemical properties, that are based on the inhibition of the right serine protease targets.

Example 4: In Vivo Assays—Dry Eye Disease

Material and Methods
 Animals
 Female Wistar rats (200-300 g, Janvier, Roubaix, France) were kept under standard pathogen-free conditions. Husbandry conditions: room temperature 20-25° C., humidity 50-60% and a day-night cycle of 12 h light/12 h dark. Food and water were available ad libitum. All in vivo manipulations were approved by the Animal Ethical Committee of the University of Antwerp (2013-67) and are in accordance to the ARRIVE guidelines for the use of animals in ophthalmic and vision research.
 Anesthesia
 To remove the exorbital lacrimal gland, animals were anesthetized with an intraperitoneal injection of 25 mg/kg ketamine (Anesketin®, Eurovet, Bladel, Netherlands) and 2.5 mg/kg xylazine (Rompun®, Bayer, Leverkusen, Germany). Routine manipulations (tear collection, fluorescein staining) were performed after induction with 5% isoflurane (Halocarbon®, New Jersey, USA), followed by a maintenance dosage of 1.5%.
 Induction of Dry Eye
 DES (Dry Eye Syndrome) was induced by removal of the exorbital lacrimal gland, located subcutaneously, on top of the masseter muscle and inferior to the nervus ophthalmicus. To remove the gland, a small incision was made beneath the right ear. The lacrimal glands of the left eye were kept intact, leaving each animal with its own individual control and eliminating the need for extra control groups. Progression of dry eye was monitored for 24 days and tear volume measurements and fluorescein staining were performed once a week. Tears were collected twice a week.
 Measurement of Aqueous Tear Production
 A phenol red thread (Zone Quick®, Menicon Co. Ltd, Nagoya, Japan) was placed in the lateral cantus of the conjunctival fornix for 15 seconds. Absorption of tear fluid resulted in a color shift from yellow to red and tear distance was measured in millimeters. Tear fluid volumes were measured once a week.
 Evaluation of Ocular Surface Damage by Fluorescein Staining
 Sodium-fluorescein (1%, Sigma-Aldrich, Seelze, Germany) in phosphate buffered saline (PBS, Gibco® by LifeTechnologies Europe, Gent, Belgium) was administered topically to the surface of the eye. To avoid false positives, eyes were rinsed after one minute with PBS and excess fluorescein was removed by placing filter paper in the lateral cantus of the eye. The eye was photographed with a microscopic lens (Photo adapter 1.0 MC 80 DX—Axiovert 25 CA, Carl Zeiss AB, Göttingen, Germany) in a darkened room under cobalt blue light. Using the Oxford fluorescein grading scale, scores from 0 to 5 were given to each eye, depending on ocular staining intensity. Semi-quantitative scoring was done in a blind manner by three independent observers. Evaluation of ocular surface damage was performed every week.
 Tear Collection
 Tear fluid was collected once a week with 10 µl capillaries (Blaubrand® Intramark, Wertheim, Germany) connected with a flexible tube to a syringe. Immediately after collection, capillaries and tear fluid were stored at −80° C., for immunological analysis.
 Tear Fluid Analysis
 TNF-α and IL-1α concentrations in tear fluid were measured flow cytometrically (FACS calibur, BD Biosciences), using Cytometric Bead Array (CBA) according to the manufacturers protocol (Rat IL-1α and TNF-α CBA flex sets, BD Biosciences, Erembodegem Belgium.
 Experimental Design
 Tear fluid was obtained twice a week. Tear volume and tissue damage was evaluated once a week. Animals were treated with Restasis® (2×/day), UAMC50, UAMC1162, UAMC1169/vehicle (2×/day) for 3 consecutive weeks. Compounds 1, 2 and 4 were formulated as follows:

| Materials | Compound 1 5 mM | Compound 2 5 mM | Compound 4 5 mM | Compound 4 500 µM |
|---|---|---|---|---|
| Compound | 2.525 mg | 3.095 mg | 3.48 mg | 3.48 mg |
| Boric acid | 20.0 mg | 20.0 mg | 20.0 mg | 200.0 mg |
| Na₂EDTA | 1.0 mg | 1.0 mg | 1.0 mg | 10.0 mg |
| Povidon K30 | 25.0 mg | 25.0 mg | 25.0 mg | 250.0 mg |
| Demineralised water | 1 ml | 1 ml | 1 ml | 10 ml |

The pH of the solutions is 4

Figure 4:
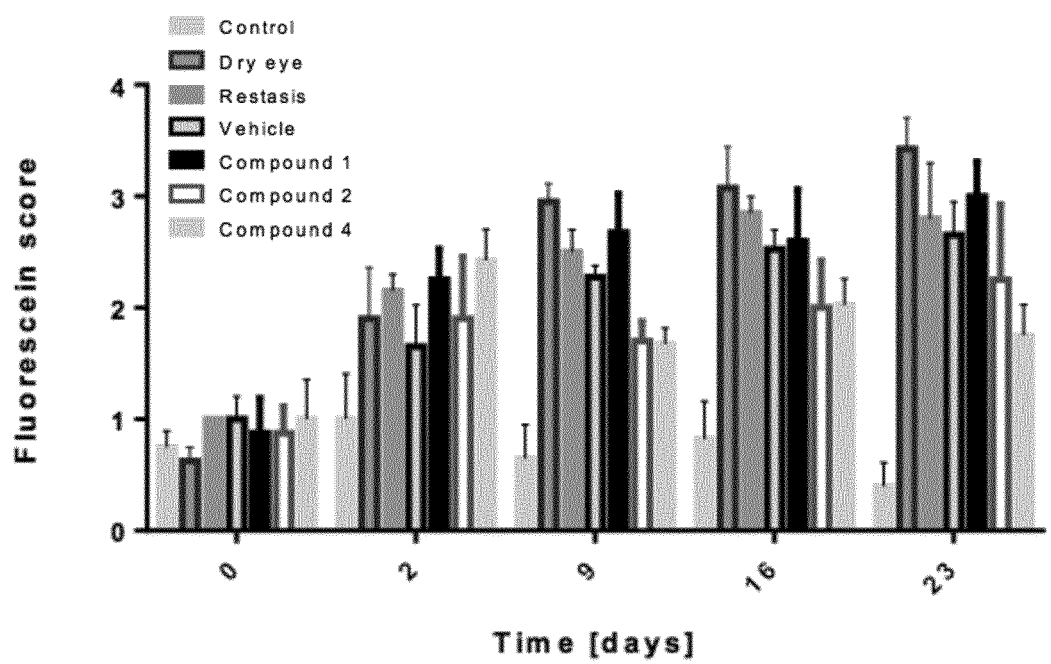
FIG. 4: Tissue damage scores of compounds 1, 2 and 4 versus control, untreated, vehicle and Restasis®.

Results
 When comparing the formulations of compound 1, 2 and 4 in this in vivo model related to ocular surface disease (see FIG. 4), and more specific to dry eye, we observed that compound 4 had a superior effect on ocular tissue damage, in comparison to the other treatments. Interestingly, compound 2 has similar effects on ocular dry eye progression based on the tissue damage parameters. However, compound 1 had no effect and showed a similar progression on tissue damage compared to dry eye group.
 Hence, compound 4 is the most promising compound based on the influence on tissue damage and was investigated further for anti-inflammatory activity related to tissue damage. In these experiments, 2 concentrations of compound 4 have been tested. A healthy control group, an untreated dry eye group, a Restasis® treated group and vehicle treated animals have been included. Treatments have been completely blinded, to avoid biased results. In both experiments, a set of clinically relevant parameters was evaluated weekly. These parameters include ocular tissue damage, tear volume and the levels of two pro-inflammatory cytokines in tear fluid. Due the method of induction of dry eye in this animal model, no significant effects have been observed on tear volume.

Evaluation of Ocular Tissue Damage of Compound 4 at 2 Different Doses

Figure 5:
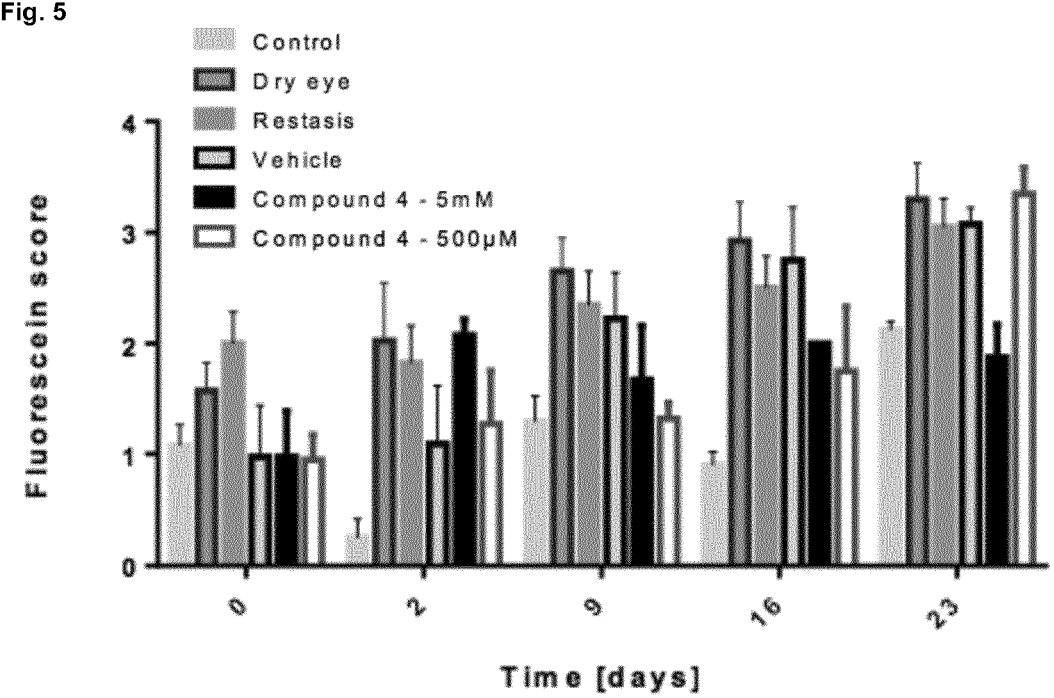
FIG. 5: Mean tissue damage scores of 2 vivo experiments±SEM of compound 4 in two different concentrations versus control, untreated, vehicle and Restasis®.

As evident from FIG. 5, compound 4 treated animals displayed again lower tissue damage scores in this follow-up experiments. Both concentrations of compound 4 seem to have a beneficial mean effect on the progression of ocular tissue damage in this animal model for dry eye, compared to untreated (dry eye) animals, vehicle treated animals and Restasis© treated animals. However, the lower dose of compound 4 failed to provide an effect on day 21. We observe this as a dose related effect.

Evaluation of Pro-Inflammatory Cytokines in Tear Fluid at Two Different Doses of Compound 4

Figure 6:
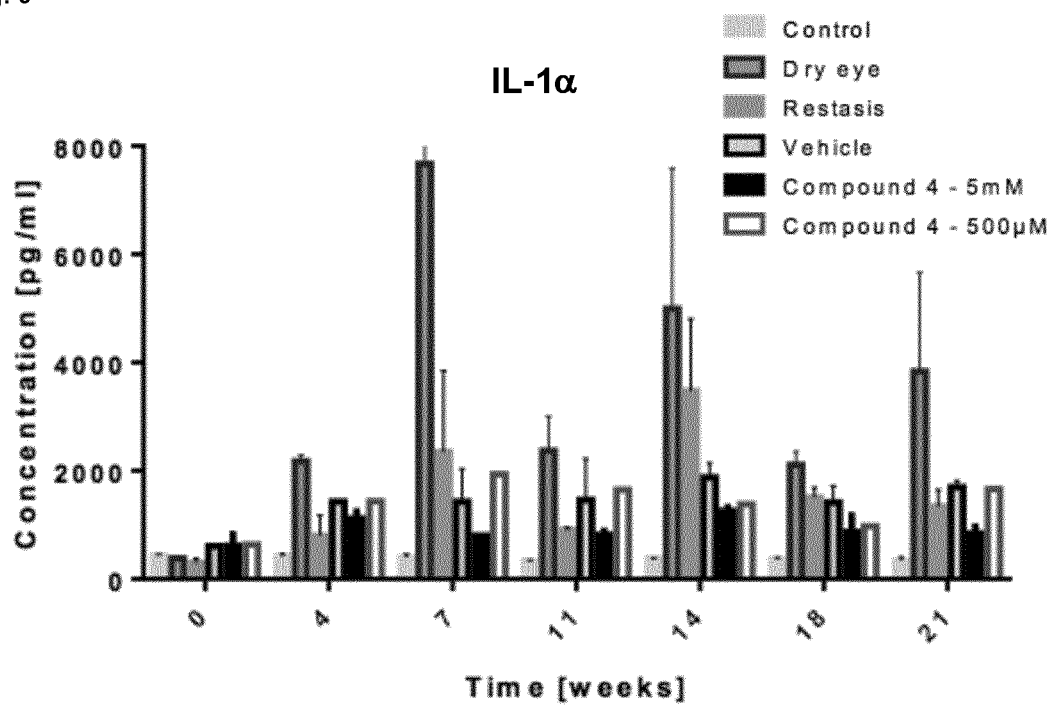
FIG. 6: Mean IL-1α concentrations of 2 vivo experiments±SEM of compound 4 in two different concentrations versus control, untreated, vehicle and Restasis®.
Figure 7:
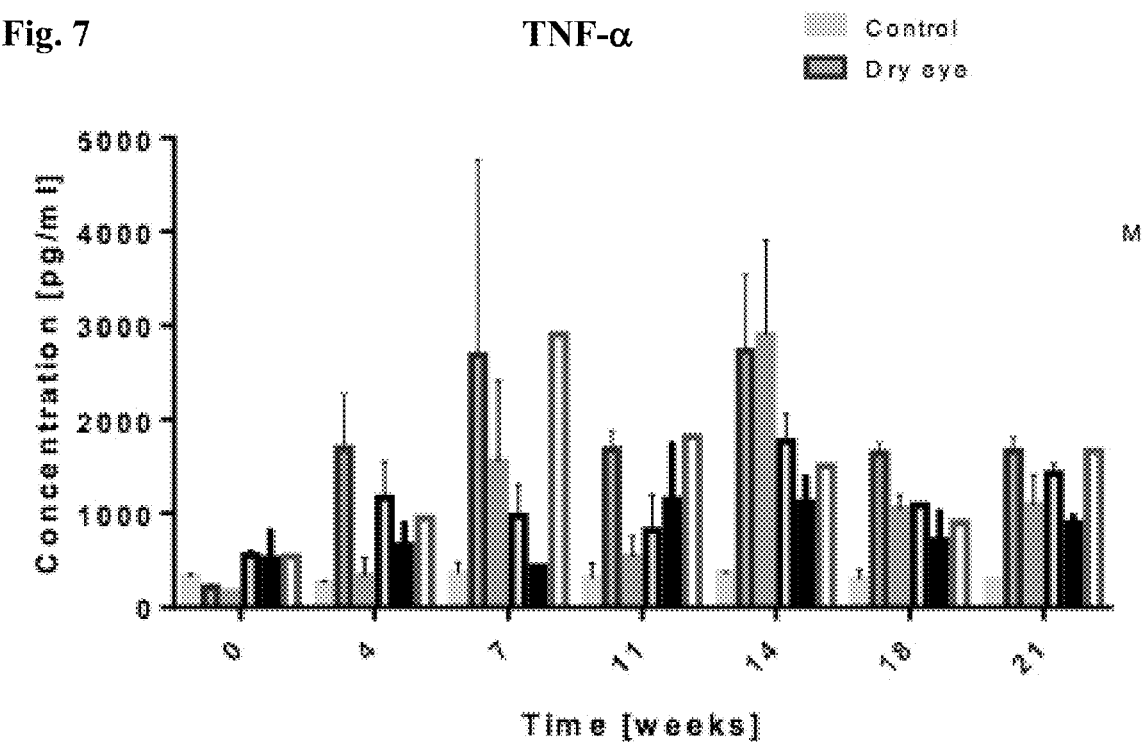
FIG. 7: Mean TNF-α concentrations of 2 vivo experiments±SEM.

Next, we have evaluated the pro-inflammatory cytokine profile in the tear fluid of the treated animals (see FIGS. 6 and 7). Again compound 4 showed an overall stronger anti-inflammatory effect and faster onset of action effect than Restasis©. Compound 4 (5 mM) is the best overall treatment. Compound 4 (5 mM) has a significant anti-inflammatory effect, in combination with a decrease in the progression of ocular damage.

Figure 8A:
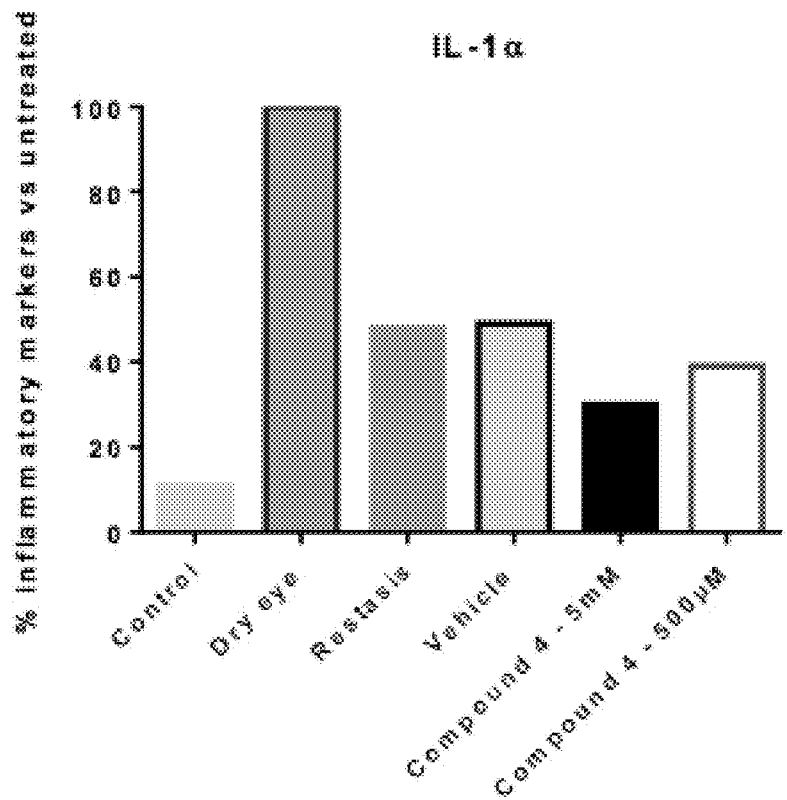
FIG. 8 A-C: IL-1α (FIG. 8A), TNF-α (FIG. 8B), and tissue damage (FIG. 8C) values of compound 4 in two different concentrations, control, vehicle and Restasis® from 7 days onward, compared relatively to untreated dry eye (100%).
Figure 8B:
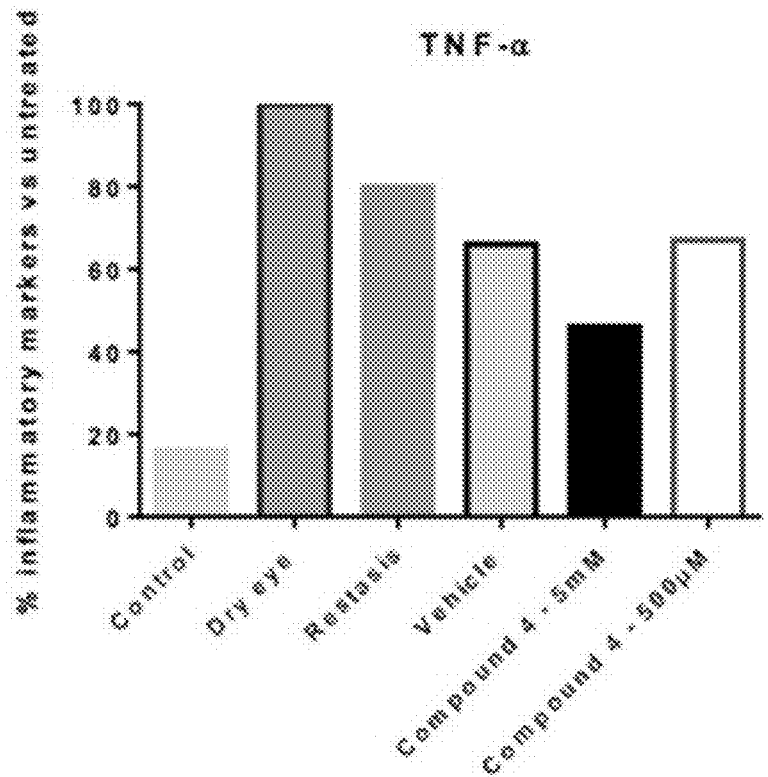
Figure 8C:
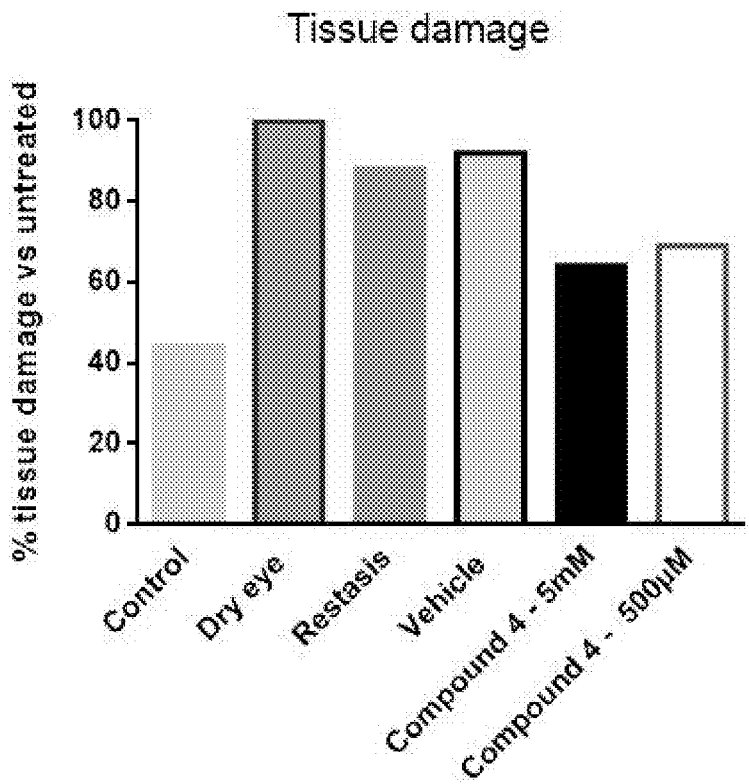

Mean Overall Effect on Dry Eye Progression of Compound 4-5 mM Versus Control, Untreated, Vehicle and Restasis©: 7 Days Post Induction of Dry Eye In these vivo experiments, dry eye is induced on day 0 and treatment starts at day 1. Dry eye severity increases in relation to time. As seen in FIG. 8 A-C, a clear distinction in treatment efficiency becomes evident after 7+ days, when dry eye severity is significantly progressed. When we investigate the results of compound 4, control, vehicle and Restasis© versus untreated dry eye from 7 days onward, the effect of compound 4 becomes even more apparent. Every treatment is compared relatively to untreated dry eye (100%).

REFERENCES

Deiteren, A. et al. "Histamine H4 and H1 receptors contribute to postinflammatory visceral hypersensitivity." *Gut* 63(12): 1873-1882.

Deiteren, A., et al. (2015). "P2X3 Receptors Mediate Visceral Hypersensitivity during Acute Chemically-Induced Colitis and in the Post-Inflammatory Phase via Different Mechanisms of Sensitization." *PLoS One* 10(4): e0123810.

Hu, J. et al. Serine protease inhibitor A3K protects rabbit corneal endothelium from barrier function disruption induced by TNF-alpha. *Investigative ophthalmology & visual science* 54, 5400-5407, doi:10.1167/iovs.12-10145 (2013).

Joossen, C. et al. Optimization and validation of an existing, surgical and robust dry eye rat model for the evaluation of therapeutic compounds. *Experimental eye research* 146, 172-178, doi:10.1016/j.exer.2016.03.006 (2016).

Joossens, J. et al. Small, potent, and selective diaryl phosphonate inhibitors for urokinase-type plasminogen activator with in vivo antimetastatic properties. *Journal of medicinal chemistry* 50, 6638-6646, doi:10.1021/jm700962j (2007).

Lin, Z. et al. Serine protease inhibitor A3K suppressed the formation of ocular surface squamous metaplasia in a mouse model of experimental dry eye. *Investigative ophthalmology & visual science* 55, 5813-5820, doi:10.1167/iovs.13-13546 (2014).

Ness, T. J., et al. (1988). "Colorectal distension as a noxious visceral stimulus: physiologic and pharmacologic characterization of pseudaffective reflexes in the rat." *Brain Res* 450(1-2): 153-169.

Thomae, D. et al. First In-111-labeled activity-based probe for SPECT imaging of uPA activity: in vivo study in human cancer xenografts. *J Labelled Compd Rad* 58, 5104-5104 (2015).

Vermeulen, W., et al. (2013). "Role of TRPV1 and TRPA1 in visceral hypersensitivity to colorectal distension during experimental colitis in rats." *Eur J Pharmacol* 698(1-3): 404-412.

The invention claimed is:

1. A method for the treatment of a PAR-related (protease-activated receptor) disorder consisting of ocular surface diseases selected from the group consisting of meibomian gland dysfunction, blepharitis, rosacea, allergies, scarring from glaucoma medications, chemical burns, thermal burns, mucous membrane pemphigoid, Sjogren's syndrome, and conjunctivitis sicca, the method comprising administering to a subject in need thereof a therapeutic effective amount of a bis(acetamidophenyl) guanidinophenylethylphosphonate compound.

2. The method according to claim 1, wherein the bis (acetamidophenyl) guanidinophenylethylphosphonate compound has formula (I):

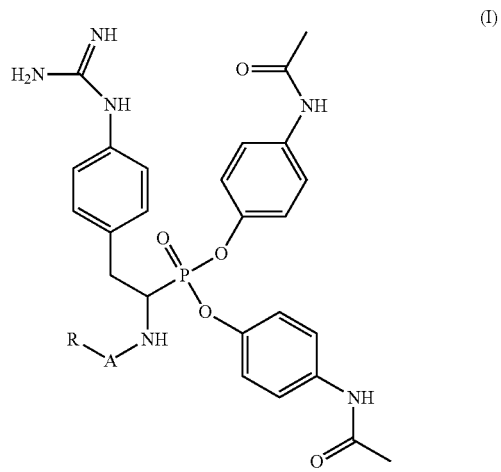

where:
A is selected from the group consisting of a direct bond, —(C═O)—, *—(C═O)—O—, *—(C═O)—NH—, and *—SO$_2$—;

R is selected from aliphatic groups or aromatic groups; and wherein the * indicates the point of attachment of A to NH.

3. The method according to claim 2, wherein:

R is selected from a 3-6 membered aromatic cycle or a —C$_{1-6}$alkyl optionally substituted with a 3-6 membered aromatic cycle.

4. The method according to claim 1, wherein the compound is Compound 2 or Compound 4:

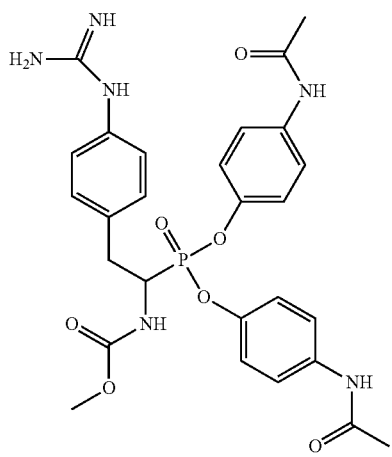

Compound 2

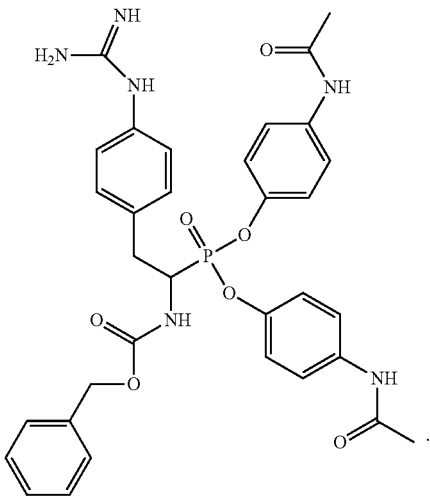

Compound 4

5. A method for the treatment of a PAR-related disorder consisting of ocular surface diseases selected from the group consisting of meibomian gland dysfunction, blepharitis, rosacea, allergies, scarring from glaucoma medications, chemical burns, thermal burns, mucous membrane pemphigoid, Sjogren's syndrome, and conjunctivitis sicca, the method comprising administering to a subject in need thereof a pharmaceutical composition, the pharmaceutical composition comprising:
   a therapeutic effective amount of a bis(acetamidophenyl) guanidinophenylethylphosphonate compound; and
   at least one pharmaceutically acceptable ingredient chosen from carriers, diluents, excipients, adjuvants, additional pharmaceutically active compounds, or combinations thereof.

* * * * *